(12) United States Patent
Lanfried

(10) Patent No.: US 8,696,352 B2
(45) Date of Patent: Apr. 15, 2014

(54) INTRA-ORAL APPLIANCE AND METHODS OF USING SAME

(75) Inventor: Judy Lanfried, Torrance, CA (US)

(73) Assignee: Lanfried Ortho Technology, LLC

( * ) Notice: Subject to any disclaimer, the term of this patent is extended or adjusted under 35 U.S.C. 154(b) by 144 days.

(21) Appl. No.: 13/233,929

(22) Filed: Sep. 15, 2011

(65) Prior Publication Data

US 2013/0071801 A1  Mar. 21, 2013

(51) Int. Cl.
*A61C 3/00* (2006.01)
*A61C 7/08* (2006.01)

(52) U.S. Cl.
USPC .................... 433/6; 433/7; 433/8; 433/24

(58) Field of Classification Search
USPC ........ 623/17.17–17.19; 433/6–11, 18–19, 24, 433/140, 229, 180–190; 128/859–862
See application file for complete search history.

(56) References Cited

U.S. PATENT DOCUMENTS

| | | | |
|---|---|---|---|
| 7,861,724 B2 | 1/2011 | Keropian | |
| 7,878,802 B2 | 2/2011 | Hagelganz et al. | |
| 7,890,193 B2 | 2/2011 | Tingey | |
| 7,905,724 B2 | 3/2011 | Kuo et al. | |
| 7,971,591 B2 | 7/2011 | Jansheski | |
| 8,444,412 B2 * | 5/2013 | Baughman et al. | 433/6 |
| 2003/0023313 A1 | 1/2003 | Byers | |
| 2003/0207224 A1 * | 11/2003 | Lotte | 433/6 |
| 2005/0126579 A1 | 6/2005 | Benja-Athon | |
| 2006/0018844 A1 | 1/2006 | Katz | |
| 2006/0172262 A1 | 8/2006 | Bruce | |
| 2007/0037120 A1 | 2/2007 | Ritter | |
| 2010/0075268 A1 * | 3/2010 | Duran Von Arx | 433/6 |
| 2012/0270173 A1 * | 10/2012 | Pumphrey et al. | 433/6 |

* cited by examiner

*Primary Examiner* — David Isabella
*Assistant Examiner* — Yashita Sharma
(74) *Attorney, Agent, or Firm* — Sughrue Mion, PLLC

(57) ABSTRACT

The present invention provides a system and method for correcting facial features and oral function in a subject. Also provided are a plurality of intra-oral appliances, which make up the system. The intra-oral appliances each include an appliance body configured for engaging one or more of the gingival-buccal area, the gingivolabial area, and the vestibular area of the subject's mouth, and include one or more extensions for at least partly defining the cavity in the vestibule of the subject's mouth.

5 Claims, 6 Drawing Sheets

INTRA-ORAL APPLIANCE AND METHODS OF USING SAME

BACKGROUND OF THE INVENTION

1. Field of the Invention

The invention relates generally to an article for correcting facial features and oral function, and more specifically to an intra oral maxillofacial prosthesis and methods for treating the symptoms of facial nerve paralysis using the same.

2. Background Information

In today's society, youth is a highly prized asset. The human face is an important element in projecting a youthful appearance, but it is always eventually subject to the effects of aging, which sagging cheeks, lines, wrinkles, folds, and depressions. Similarly, these effects may occur after extreme, rapid weight loss, or as a consequence of facial paralysis from health problems such as Bell's palsy or stroke.

Bell's Palsy is a form of facial paralysis resulting from dysfunction cranial nerve VII (the facial nerve) that results in the inability to control facial muscles on the affected side. The annual incidence of Bell's palsy is about 20 per 100,000 population, and the incidence increases with age. Bell's palsy is defined as an idiopathic unilateral facial nerve paralysis, usually self-limiting. The hallmark of this condition is a rapid onset of partial or complete palsy (paralysis) that often occurs overnight. In rare cases, it can occur bilaterally resulting in total facial paralysis. Symptoms vary from person to person and can range in severity from mild weakness to total paralysis. These symptoms include twitching, weakness, or paralysis, drooping eyelid or corner of the mouth, drooling, dry eye or mouth, impairment of taste, and excessive tearing in the eye. For most people, Bell's palsy symptoms improve within a few weeks, with complete recovery in three to six months. About 10 percent will experience a recurrence of Bell's palsy, sometimes on the other side of the face. A small number of people continue to have some Bell's palsy signs and symptoms for life.

The resultant effects of facial paralysis include, but are not limited to, facial distortion/disfigurement, psychological trauma, problems with mastication and eating, and the inability to smile and/or talk normally. Because oral tissues are highly sensitized, they often become irritated due to food being trapped in the cheek of a person afflicted with facial paralysis. In addition, air bubbles accumulate in the oral vestibule on the affected side of the mouth when speaking.

Various forms of paralysis or weakness of the unilateral or bilateral facial muscles have been caused by injury to the facial nerve, viral infection, bacterial infection, nerve trauma, vascular etiologies, parotidectomy, stroke, brain surgery, aging, and trauma etiologies. Because facial paralysis affects each individual differently, afflicted subjects must seek treatments tailored to the specific symptoms that occur. Drugs are commonly used to treat the condition chemically, while various forms of surgery attempt to transplant nerves from other areas of the face and body and/or attempt to lift drooping skin/cheeks. In addition, subjects afflicted with facial palsy often seek speech therapy to correct basic communication skills.

Thus, a need exists for a system that addresses the physical appearance, oral discomfort and psychological distress from the victims' physical affect of the traumatic neuropathy.

SUMMARY OF THE INVENTION

The present invention is based on the finding that an intra-oral prosthesis can be used to correct facial features and/or oral function of a subject suffering from facial palsy. Provided herein are a system and method for correcting facial features and oral function of a subject. Using accurate models of both upper and lower arches of a subject's teeth, including the full vestibular areas, the appliances discussed herein are custom designed and built with regard to the individual subject's unique dentition and oral structure. Accordingly, the systems and methods provided herein include one or more intra-oral prosthesis for the relief of symptoms and physical, psychological and social affect of the subject's palsy or defect.

As such, in one aspect, the invention provides an intra-oral appliance for correcting facial features of a subject. The appliance includes an appliance body configured for engagement with a subject's upper teeth and anterior palate, wherein the appliance body has one or more extensions for engaging one or more of the gingival-buccal area and the vestibular area of the subject's mouth, thereby at least partly defining a cavity in the vestibule of the subject's mouth. In one embodiment, the appliance body has one extension for defining the vestibule at either side of the subject's mouth. In another embodiment, the appliance body has two extensions for defining the vestibule at both sides of the subject's mouth.

In another aspect, the invention provides a system for correcting facial features of a subject. The system includes an upper intra-oral appliance comprising a first appliance body configured for engaging one or more of the upper gingival-buccal area, the upper gingivolabial area, and the upper vestibular area of the subject's mouth, and a lower intra-oral appliance comprising a second appliance body configured for engaging one or more of the lower gingival-buccal area, the lower gingivolabial area, and the lower vestibular area of the afflicted side the subject's face. In one embodiment, the first appliance body is configured for engagement with the subject's upper teeth and anterior palate, wherein the first appliance body has one or more extensions for engaging one or more of the upper gingival-buccal area, the upper gingivolabial area, and the upper vestibular area of the subject's mouth. In another embodiment, the first appliance body is configured for engagement with the subject's upper gingiva on the afflicted side the subject's face, wherein the first appliance body is positioned from the maxillary midline of the subject's upper gingiva to the farthest upper posterior tooth or edentulous buccal portion. In yet another embodiment, the first appliance body is configured for engaging the upper gingiva where the tooth crown meets the gum line. In yet another embodiment, the first appliance body further comprises one or more posterior lingual/palatal claps for engaging one or more teeth of the subject. In yet another embodiment, the second appliance body is configured for positioning from the mandibular midline of the subject's lower gingival to the farthest lower posterior tooth or edentulous buccal portion. In yet another embodiment, the second appliance body further comprises one or more posterior lingual/palatal claps for engaging one or more teeth of the subject.

In another embodiment, the system further includes a third intra-oral appliance comprising a third appliance body configured for engagement with the subject's upper gingiva on the afflicted side the subject's face, wherein when used, the third appliance body is positioned from the maxillary midline of the subject's upper gingiva to the farthest upper posterior tooth or edentulous buccal portion, and wherein the first and third intra-oral appliances are not used simultaneously.

In another aspect, the invention provides a system for correcting facial features of a subject. The system includes a first upper intra-oral appliance comprising a first appliance body configured for engagement with the subject's upper teeth and anterior palate, wherein the first appliance body has one or more extensions for engaging one or more of the upper gingival-buccal area, the upper gingivolabial area, and the upper vestibular area of the subject's mouth, a second upper intra-oral appliance comprising a second appliance body configured for engagement with the subject's upper gingiva on the afflicted side the subject's face, wherein the second appliance body is positioned from the maxillary midline of the subject's upper gingiva to the farthest upper posterior tooth or edentulous buccal portion, and a lower intra-oral appliance comprising a third appliance body configured for engaging one or more of the lower gingival-buccal area, the lower gingivolabial area, and the lower vestibular area of the afflicted side the subject's face, wherein the first upper intra-oral appliance and the second upper intra-oral appliances are not used simultaneously. In one embodiment, any of the first appliance body, the second appliance body, and the third appliance body independently further comprise one or more posterior lingual/palatal clasps for engaging one or more teeth of the subject.

In another aspect, the invention provides a method for correcting facial features and oral function of a subject. The method includes fitting a subject in need thereof with an intra-oral appliance, which includes an appliance body configured for engagement with a subject's upper teeth and anterior palate, wherein the appliance body has one or more extensions for engaging one or more of the gingival-buccal area, the gingivolabial area, and the vestibular area of the subject's mouth, thereby at least partly defining the cavity in the vestibule of the subject's mouth.

In another aspect, the invention provides a method for correcting facial features and oral function of a subject. The method includes fitting a subject in need thereof with an upper intra-oral appliance comprising a first appliance body configured for engaging one or more of the upper gingival-buccal area, the upper gingivolabial area, and the upper vestibular area of the subject's mouth, and a lower intra-oral appliance comprising a second appliance body configured for engaging one or more of the lower gingival-buccal area, the lower gingivolabial area, and the lower vestibular area of the afflicted side the subject's face, thereby at least partly defining the cavity in the vestibule of the subject's mouth.

In one embodiment, the first appliance body is configured for engagement with the subject's upper teeth and anterior palate, wherein the first appliance body has one or more extensions for engaging one or more of the upper gingival-buccal area, the upper gingivolabial area and the upper vestibular area of the subject's mouth. In another embodiment, the first appliance body is configured for engagement with the subject's upper gingiva on the afflicted side the subject's face, wherein the first appliance body is positioned from the maxillary midline of the subject's upper gingiva to the farthest upper posterior tooth or edentulous buccal portion. In yet another embodiment, the first appliance body is configured for engaging the upper gingiva where the tooth crown meets the gum line. In yet another embodiment, the first appliance body further comprises one or more posterior lingual/palatal clasps for engaging one or more teeth of the subject. In yet another embodiment, the second appliance body is configured for positioning from the mandibular midline of the subject's lower gingival to the farthest lower posterior tooth or edentulous buccal portion. In yet another embodiment, the second appliance body further comprises one or more posterior lingual clasps for engaging one or more teeth of the subject.

In certain embodiments, the subject suffers from facial paralysis or defect. In those embodiments, the facial paralysis or defect is a result of brain surgery, glioma, brain injury, facial or dental surgery, Bell's Palsy, neuro-injuries, aging, stroke or disease.

DETAILED DESCRIPTION OF THE INVENTION

Figure 1:
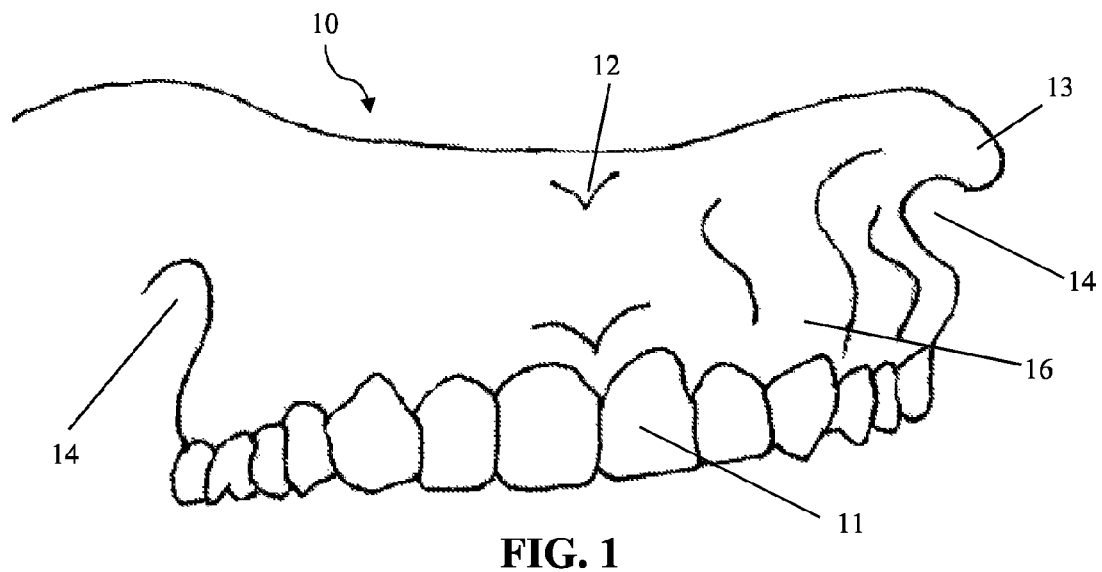
FIG. 1 is a frontal view of the maxillary arch and upper teeth.

Before the present systems, devices, and methods are described, it is to be understood that this invention is not limited to particular devices, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention devices and methods corresponding to the scope of each of these phrases. Thus, a device or method comprising recited elements or steps contemplates particular embodiments in which the device or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is based on the finding that an intra-oral prosthesis can be used to correct facial features and/or oral function of a subject suffering from facial palsy. Thus, provided herein is a system for correcting facial features of a subject. The system includes one or more intra-oral appliances, which can be used simultaneously or individually by a subject to at least partially define the cavity in the vestibule of the subject's mouth. In one embodiment, the system includes two or more intra-oral appliances. In another embodiment, the system includes three or more intra-oral appliances, which hereinafter will be referred to as Appliance A, Appliance B, and Appliance C, as discussed below.

Each of Appliances A-C are custom fit to each subject by making a mold or dental impression of the upper and lower teeth and palate. The appliances are then made using any of commonly used biocompatible dental materials such as, but not limited to, polyurethane, polycarbonate, heat- or cold-cured acrylics, fibered acrylic plastic, thermoplastic polyurethane, flexible polymers, any suitable chemically activated or light activated materials that cure to solid form, or any combination thereof. Thus, suitable biocompatible dental plastics from which Appliances A-C may be made include, but are not limited to, thermoplastics, polyethylene, polystyrene, polyvinyl chloride, polytetrafluoroethylene, acrylics, polyesters, silicones, polyurethanes, and/or halogenated plastics or the like. In various embodiments, Appliances A-C may molded or laminated from multiple layers of one or more of the biocompatible dental materials, depending on the needs of the user. In other embodiments, Appliances A-C may have a solid core, such as a biocompatible metal, surrounded by the one or more biocompatible dental materials. In yet other embodiments, the materials from which Appliances A-C may be made, can be clear or colored, depending on the needs of the user. In one embodiment, any or all of Appliances A-C are made from ethylene vinyl acetate, either alone or in combination with any other biocompatible dental material.

Referring now to FIG. 1, there is shown a human maxilla 10 with upper teeth 11. As shown, the cheek 13 is pulled away from the maxilla exposing a hollow space within the gingival-buccal area 14 of the vestibule of the mouth into which air can become trapped in subjects having facial palsy. During normal speech of persons not having a facial palsy, the enervated muscle within cheek 13 forces air from gingival-buccal area 14. Also shown is gingival firm tissue 16 covering the bony structure of the maxilla and the roots (not shown) of the upper teeth 11. The gingival firm tissue 16 typically has one or more small protuberances or projections (papilla) 12 on the surface thereof.

As used herein, the term "gingiva" refers to the gums of a subject. As used herein, the term "buccal" is used to refer to the cheek or sides of the mouth. Thus, the term "gingival-buccal area" of a subject refers to the area within a subject's mouth that is defined by the gums and the cheek.

As used herein, the term "labium" refers to the lip of a subject. Thus, the term "gingivolabial area" refers to the area within a subject's mouth that is defined by the gums and the inner surface of the lips.

As used herein, the term "vestibule" refers any of various cavities or hollows within the mouth of subject. Thus, the term "vestibular area" is used to refer to any cavity or hollow within the subject's mouth that is located within the gingival-buccal areas and/or the gingivolabial areas of the mouth.

Figure 2A:
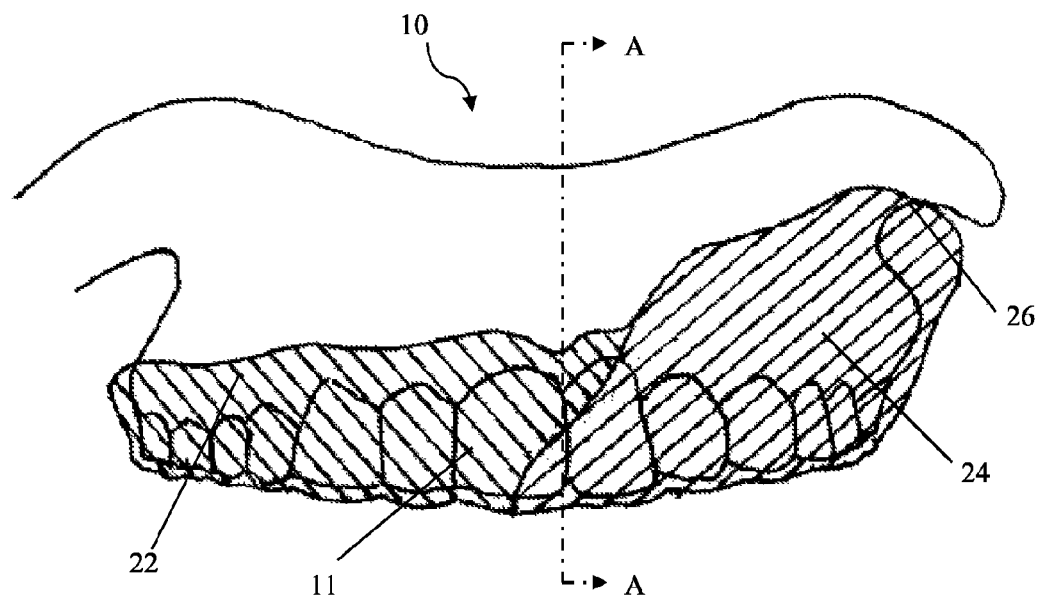
FIGS. 2A-2D are frontal and occlusal views of a human maxilla and upper teeth, showing Appliance A in place over the upper teeth.
Figure 2B:
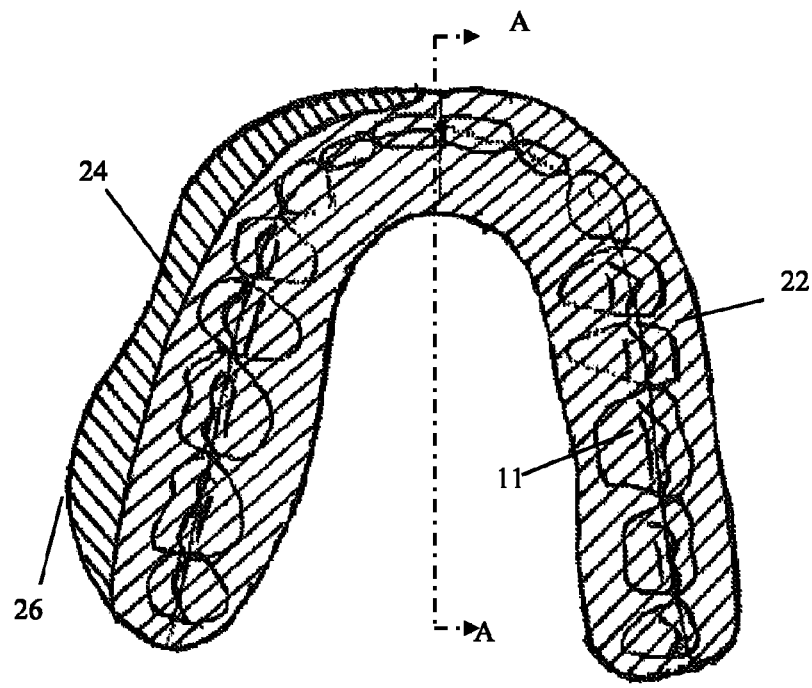

Referring now to FIGS. 2A and 2B, there is shown an embodiment of intra-oral Appliance A, which includes an appliance body 22 fitted over the upper teeth 11 of a human maxilla 10. The appliance body 22 may be generally configured like a prior art orthodontic retainer, and can be made of hard or soft plastic or other suitable materials. Body 22 fits snugly against and covers the anterior palate, or roof of the mouth, and is generally U-shaped (as shown in FIG. 2B). Body 22 is custom-fitted to fit over the subjects upper teeth in the same manner as an occlusal night guard, which uses occlusal coverage to hold the appliance body 22 firmly onto the upper teeth of the subject. Depending on the severity of the subject's facial palsy, body 22 may have a thicker portion 24, which begins at the maxillary midline A-A of the subject's upper gingiva and extends to the farthest upper posterior tooth or edentulous buccal portion. It should be understood that the thickness of thicker portion 24 may not be constant, and in most instances, can resemble the thickness of body 22 at the maxillary midline and increase to its thickest point at the farthest upper posterior tooth or edentulous buccal portion of the mouth. Thicker portion 24 includes at least one extension 26 for engaging one or more of the upper gingival-buccal area, the upper gingivolabial area, and the upper vestibular area of the subject's mouth. Thus, extension 26 defines the cavity in the vestibule of the subject's mouth on the side afflicted with facial palsy.

Figure 2C:
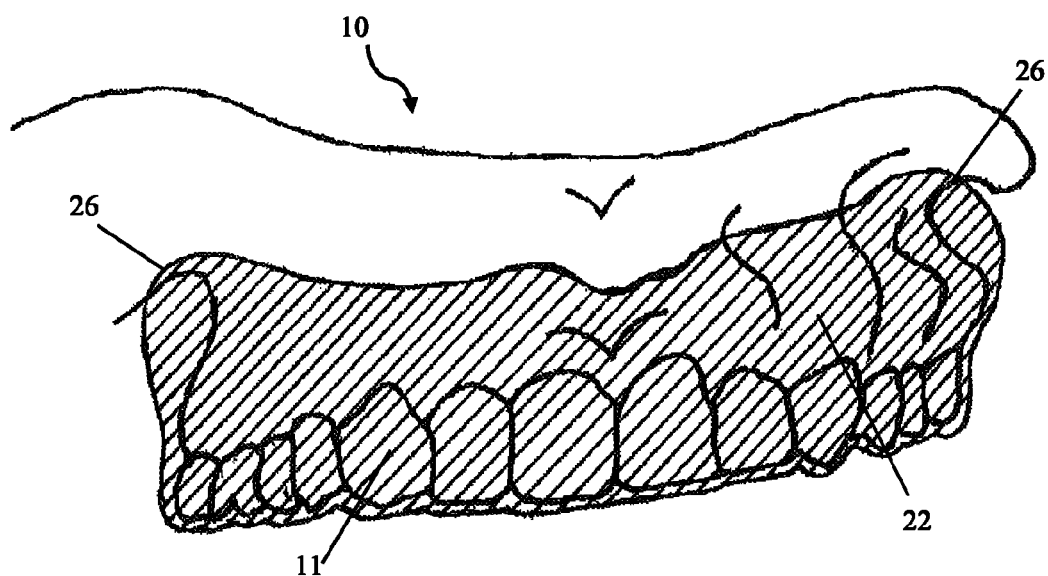
Figure 2D:
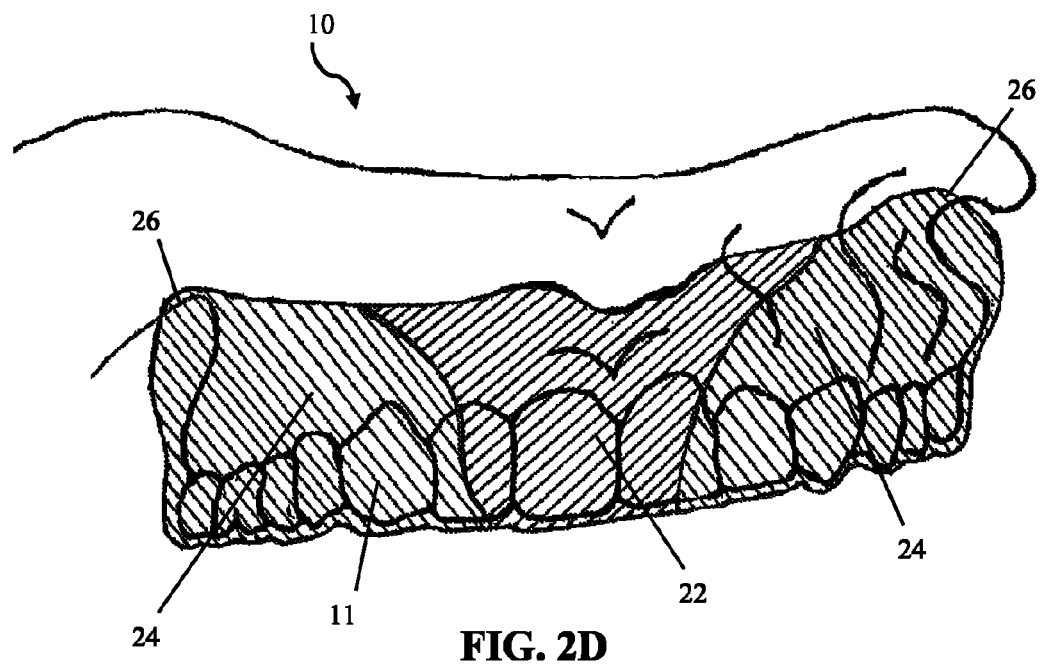

FIGS. 2C and 2D show embodiments of intra-oral Appliance A for use when the subject is afflicted with bilateral facial palsy. FIG. 2C shows body 22 with two extensions 26 for engaging the upper gingival-buccal area, the upper gingivolabial area, and the upper vestibular area on both sides of the subject's mouth. In this embodiment, body 22 does not have one or more thicker portions 24, but rather, extensions 26 extend directly from body 26. FIG. 2D shows an embodiment wherein body 22 is configured with two thicker portions 24, the extensions 26 of which would be used to engage the upper gingival-buccal areas, the upper gingivolabial areas, and/or the upper vestibular areas on both sides of the subject's mouth.

In most instances, body 22 is held in place by engagement with the upper teeth and anterior palate of the subject. However, in certain embodiments, body 22 can have one or more posterior lingual/palatal clasps (not shown), which are usually made of stainless steel, for engaging one or more of the subject's teeth. It should be understood that any of the intra-oral clasps known in the art for dental appliances may be integrated into body 22 for additional security of the device when worn by the subject. Exemplary clasps include, but are not limited to c-clasps, which are placed over and surround a molar, ball clasps, which are placed between teeth and have a ball on the gingival side for securing the appliance in place, and Adams' clasps, which are formed wire clasps of modified arrowhead design using the buccomesial and distoproximal undercuts of a tooth for retention.

Figure 3A:
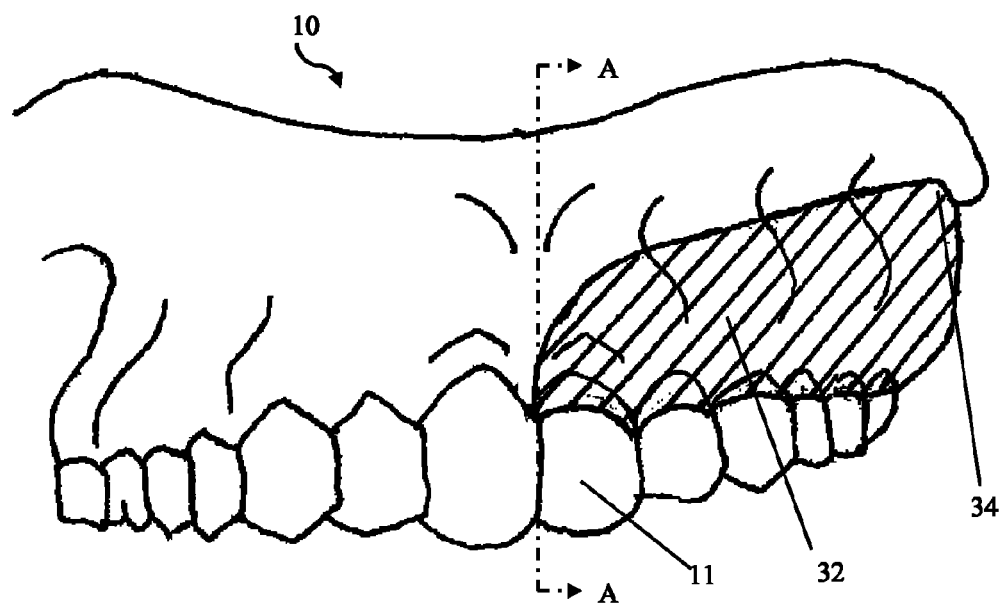
FIG. 3A is a frontal view of a human maxilla and upper teeth, showing Appliance B in place over the upper gingiva on the afflicted side of the face.
Figure 3B:
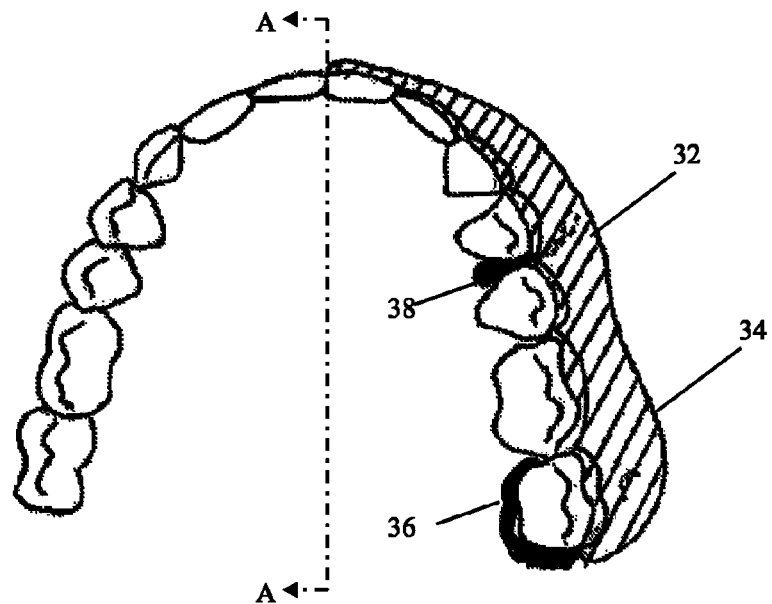
FIG. 3B is a bottom view of the human maxilla and upper teeth, showing Appliance B in place from the maxillary midline of the upper gingiva to the farthest upper posterior tooth or edentulous buccal portion.

Referring now to FIGS. 3A and 3B, there is shown an embodiment of intra-oral Appliance B, which includes an appliance body 32 fitted over the upper teeth 11 of a human maxilla 10. The appliance body 32 may be generally configured like a prior art orthodontic retainer, and can be made of hard or soft plastic or other suitable materials. Body 32 is configured for engaging the upper gingiva where the tooth crown meets the gum line on the afflicted side of the subject's face. Body 32 is configured for positioning from the maxillary midline A-A of the subject's upper gingiva to the farthest upper posterior tooth or edentulous buccal portion of the subject's mouth, and includes at least one extension 34 for engaging one or more of the upper gingival-buccal area, the upper gingivolabial area, and the upper vestibular area of the subject's mouth. The at least one extension 34 defines the cavity in the vestibule of the subject's mouth on the side afflicted with facial palsy.

Figure 3C:
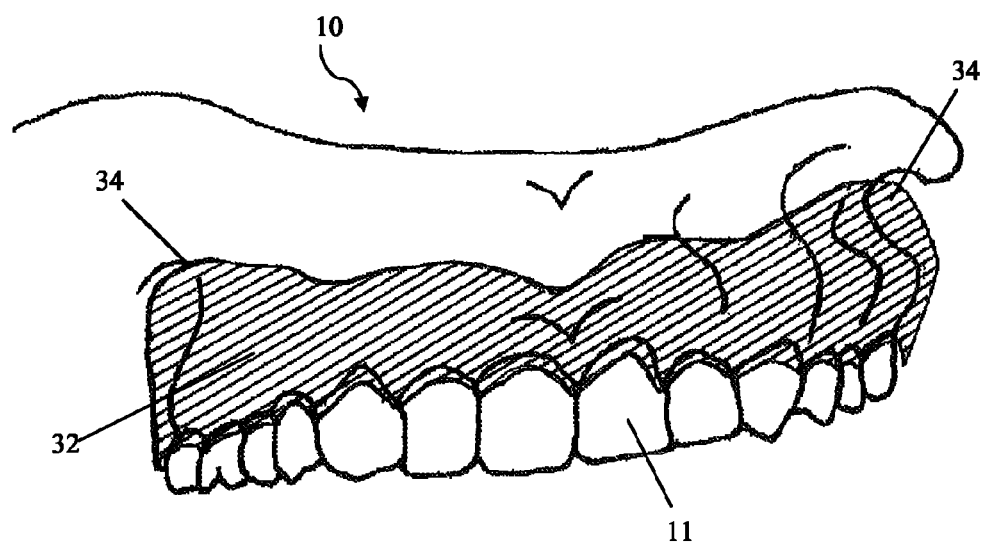
FIG. 3C is a frontal view of a human maxilla and upper teeth, showing another embodiment of Appliance B in place over the upper gingiva when the subject is afflicted with bilateral facial palsy.

FIG. 3C shows an embodiment of intra-oral Appliance B for use when the subject is afflicted with bilateral facial palsy. In this embodiment, body 32 is configured for fitment over all of the subject's upper teeth (similar to a conventional dental retainer) with extensions 34 defining the cavities in the vestibule on both sides of the subject's mouth. In another embodiment, body 32 may have one or more thicker portions (not shown) for further correcting facial features and/or oral function of the subject. It should be understood that in certain instances, more than one intra-oral Appliance B (as shown in FIGS. 3A and 3B) may be worn by the user, rather than the single bilateral embodiment shown in FIG. 3C, to engage the upper gingival-buccal areas, the upper gingivolabial areas, and/or the upper vestibular areas on both sides of the subject's mouth.

In various embodiments, body 32 is held in place by one or more posterior lingual/palatal clasps 36 and 38 (as shown in FIG. 3B), which are usually made of stainless steel, for engaging one or more of the subject's teeth. Exemplary clasps include, but are not limited to c-clasps 36, which are placed over and surround a molar, ball clasps 38, which are placed between teeth and have a ball on the gingival side for securing the appliance in place, and Adams' clasps (not shown). In most instances, such posterior lingual/palatal clasps are embedded within body 32 at the time that the body is formed.

It should be understood that Appliance A and Appliance B are not intended to be worn simultaneously by the subject. When a subject is prescribed or otherwise obtains a system in which both Appliance A and Appliance B are provided, the subject may select the Appliance that best suit's the needs of the user. For example, the subject may find that Appliance A is more comfortable for daily usage, but Appliance B is preferable for social occasions because it is less noticeable and more natural looking when worn.

Figure 4A:
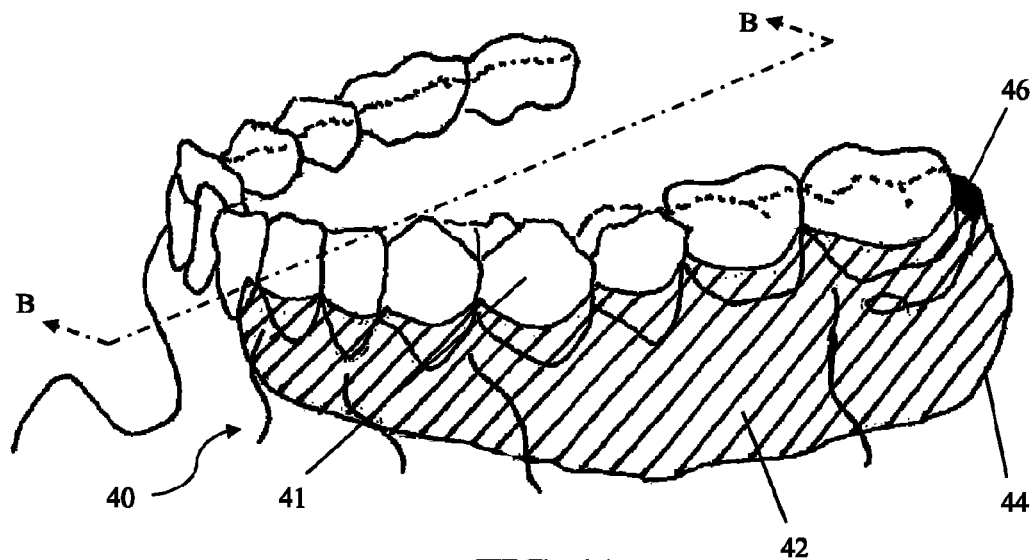
FIG. 4A is a frontal view of the human mandible and lower teeth, showing Appliance C in place over the lower gingiva on the afflicted side of the face.
Figure 4B:
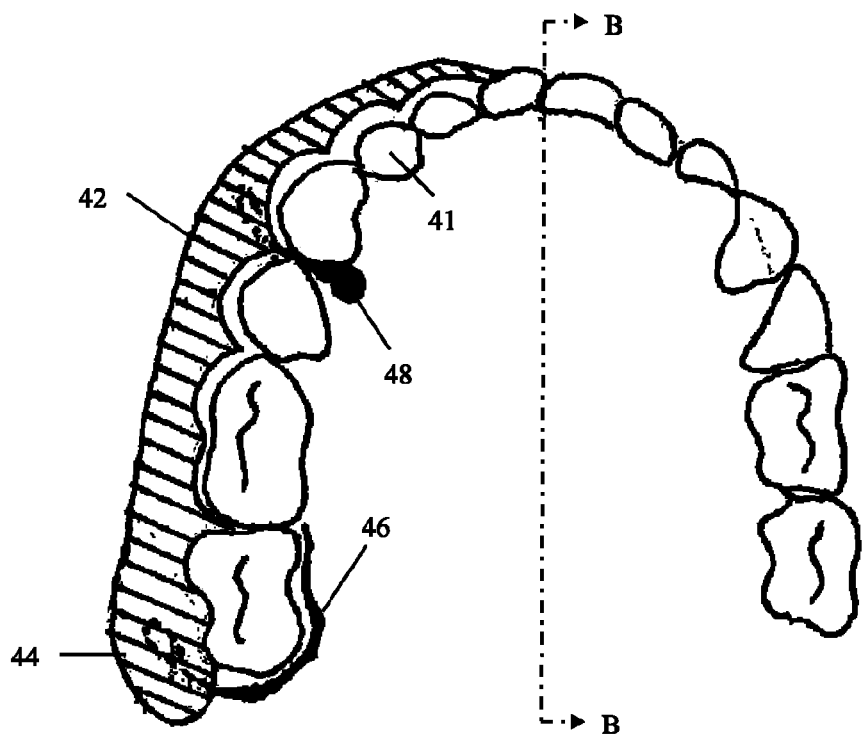
FIG. 4B is a top view of the human mandible and lower teeth, showing Appliance C in place from the mandibular midline of the lower gingiva to the farthest lower posterior tooth or edentulous buccal portion.

Referring now to FIGS. 4A and 4B, there is shown an embodiment of lower intra-oral Appliance C, which includes an appliance body 42 fitted over the lower teeth 41 of a human mandible 40. The appliance body 42 may be generally configured like a prior art orthodontic retainer, and can be made of hard or soft plastic or other suitable materials. Body 42 is configured for engaging the lower gingiva where the tooth crown meets the gum line on the afflicted side of the subject's face. Body 42 is further configured for positioning from the mandibular midline B-B of the subject's lower gingiva to the farthest lower posterior tooth or edentulous buccal portion of the subject's mouth, and includes at least one extension 44 for engaging one or more of the lower gingival-buccal area, the lower gingivolabial area, and the lower vestibular area of the subject's mouth. The at least one extension 44 defines the lower cavity in the vestibule of the subject's mouth on the side afflicted with facial palsy.

Figure 4C:
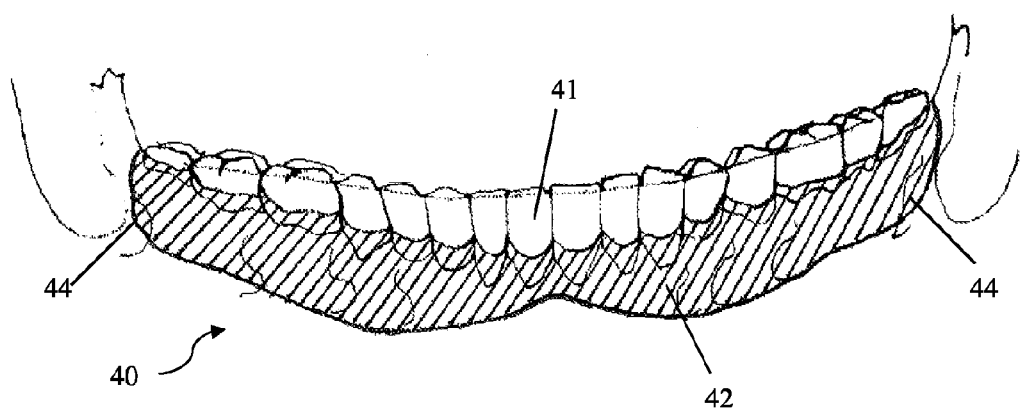
FIG. 4C is a frontal view of a human mandible and lower teeth, showing another embodiment of Appliance C in place over the lower gingiva when the subject is afflicted with bilateral facial palsy.

FIG. 4C shows an embodiment of intra-oral Appliance C for use when the subject is afflicted with bilateral facial palsy. In this embodiment, body 42 is configured for fitment over all of the subject's lower teeth 41 (similar to a conventional dental retainer) with two extensions 44 defining the cavities in the lower vestibules on both sides of the subject's mouth. In another embodiment, body 42 may have one or more thicker portions (not shown) for further correcting facial features and/or oral function of the subject. It should be understood that in certain instances, more than one intra-oral Appliance C (as shown in FIGS. 4A and 4B) may be worn by the user, rather than the single bilateral embodiment shown in FIG. 4C, to engage the lower gingival-buccal areas, the lower gingivolabial areas, and/or the lower vestibular areas on both sides of the subject's mouth.

In various embodiments, body 42 is held in place by one or more posterior lingual clasps 46 and 48 (shown in FIGS. 4A and 4B), which are usually made of stainless steel, for engaging one or more of the subject's teeth. Exemplary clasps include, but are not limited to c-clasps 46, which are placed over and surround a molar, ball clasps 48, which are placed between teeth and have a ball on the gingival side for securing the appliance in place, and Adams' clasps (not shown). In most instances, such posterior lingual/palatal clasps are embedded within body 42 at the time that the body is formed.

When a subject is prescribed or otherwise obtains a system in which Appliances A, B and C are provided, the subject may select any combination of Appliances that best suit's the needs of the user. For example, the subject may find that Appliance A in combination with Appliance C sufficiently corrects facial features and oral function for daily usage, but Appliance B in combination with Appliance C is preferable for social occasions because, as indicated above, Appliance B is less noticeable and more natural looking when worn than Appliance A.

Accordingly, in another aspect, the invention provides a method for correcting facial features and oral function of a subject. The method includes fitting a subject in need thereof with one or more of the intra-oral appliance defined above. As used herein, the term "subject" refers to any individual or patient to which the subject methods are performed. Generally the subject is human, although as will be appreciated by those in the art, the subject may be an animal that is used as a model for facial palsy. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Various forms of paralysis or weakness of the unilateral or bilateral facial muscles have been caused by injury to the facial nerve, viral infection, bacterial infection, nerve trauma, vascular etiologies, parotidectomy, stroke, brain surgery, aging, and trauma etiologies. Thus, subjects upon which the methods of the invention may be performed include, but are not limited to, those suffering from facial paralysis or defect. Such facial paralysis or defect may result from any one or more of brain surgery, glioma, brain injury, facial or dental surgery, Bell's Palsy, neuro-injuries, aging, stroke or disease.

In addition, as humans age, the natural facial muscle tone and/or skin tension lessens, thereby resulting in a slight (or in some cases severe) drooping of the cheek. Thus, the methods provided herein find use in correcting facial features of older subjects who do not have facial palsy.

In all instances, the definition of the upper and/or lower vestibule by the one or more extensions of the appliance bodies described herein, serve to plump or otherwise lift and/or stretch the cheek tissue along the mandibular jaw and gingival ridge. This results in a straightening of the lip line, balancing of a slacked facial aspect, and improving oral function of the subject. Thus, the systems and intra-oral appliances described herein serve to treat oral dysfunction, physical affect, and psychological perception of self in a subject having facial palsy. Abnormal speech, if present, is aided in that any air that is trapped and/or bubbling within the upper and/or lower vestibules between the cheek and the gingiva on the afflicted side of the face is reduced by filling the void from lost muscle tension and allowing the air to flow over the tongue instead of being redirected to the collapsed vestibule. In addition, mastication of food is improved by preventing the pocketing of food particles in the vestibule of the cheek. A more natural contour of the vestibule aids in the downward drainage of saliva to the occlusal surface of the mandibular arch, aiding the elimination of oral fluids from the mouth. In certain subjects, the pooling of saliva can cause irritation of the gingival firm tissue, thereby causing sores on the lips and corners of the mouth.

Although the invention has been described with reference to the above appliances, it will be understood that modifications and variations are encompassed within the spirit and scope of the invention. Accordingly, the invention is limited only by the following claims.

I claim:

1. A system for correcting facial features of a subject afflicted with facial paralysis on one or both sides of the face, comprising:
   a) a first upper intra-oral appliance comprising a first appliance body configured for engagement with the subject's upper teeth and anterior palate, wherein the first appliance body has one or more extensions protruding from an area corresponding to the upper gingiva of the subject for engaging one or more of the upper gingival-buccal area, the upper gingivolabial area, and the upper vestibular area of the subject's mouth;
   b) a second upper intra-oral appliance comprising a second appliance body configured for engagement with the subject's upper gingiva and buccal dentition on the afflicted side the subject's face, wherein the second appliance body is positioned from the maxillary midline of the subject's upper gingiva to the farthest upper posterior tooth or edentulous buccal portion, and wherein the second appliance body has one or more extensions protruding from an area corresponding to the upper gingiva of the subject for engaging one or more of the upper gingival-buccal area, the upper gingivolabial area, and the upper vestibular area of the subject's mouth; and
   c) a lower intra-oral appliance comprising a third appliance body configured for engagement with the subject's lower gingiva and buccal dentition on the afflicted side of the subject's face, wherein the third appliance body has one or more extensions protruding from an area corresponding to the lower gingiva of the subject for engaging one or more of the lower gingival-buccal area, the lower gingivolabial area, and the lower vestibular area of the afflicted side the subject's face,
   wherein the first upper intra-oral appliance and the second upper intra-oral appliances are not used simultaneously.

2. The system of claim 1, wherein any of the first appliance body, the second appliance body, and the third appliance body independently further comprise one or more posterior lingual/palatal clasps for engaging one or more teeth of the subject.

3. The system of claim 1, wherein each of the first, second, and third appliance bodies have one extension for defining the vestibule of the mouth on the afflicted side of the subject's face.

4. The system of claim 1, wherein the second appliance body is positioned over the entire upper gingiva and posterior buccal dentition of the subject.

5. The intra-oral appliance of claim 4, wherein each of the first, second, and third appliance bodies have two extensions for defining the vestibule of the mouth on both sides of the subject's face.

* * * * *